United States Patent [19]

Schreck

[11] 4,411,655
[45] Oct. 25, 1983

[54] APPARATUS AND METHOD FOR PERCUTANEOUS CATHETERIZATION

[76] Inventor: David M. Schreck, 14 Sylvan Ter., Summit, N.J. 07901

[21] Appl. No.: 325,848

[22] Filed: Nov. 30, 1981

[51] Int. Cl.³ .................... A61M 5/00; A61M 29/00
[52] U.S. Cl. .................. 604/165; 604/104; 604/281; 285/381
[58] Field of Search ............. 128/214.4, 214 R, 343, 128/348–350; 285/381; 604/104, 164, 165, 281

[56] References Cited

U.S. PATENT DOCUMENTS

| | | | |
|---|---|---|---|
| 3,606,592 | 9/1971 | Madurski et al. | 3/1.7 |
| 3,786,806 | 1/1974 | Johnson et al. | 128/92 D |
| 3,788,318 | 1/1974 | Kim et al. | 128/214.4 |
| 4,170,990 | 10/1979 | Baumgart et al. | 128/92 G |
| 4,296,955 | 10/1981 | Martin | 285/381 |

Primary Examiner—Stephen C. Pellegrino

[57] ABSTRACT

An apparatus for percutaneous catheterization of a vascular or other body compartment employs a shape memory alloy cylindrical cannula which expands after introduction into the body compartment with sufficient radial force to dilate the vascular member. A cylindrical plastic sheath embracing the cannula facilitates introduction and insulates the vascular compartment from contact with the metal of the cannula.

10 Claims, 2 Drawing Figures

APPARATUS AND METHOD FOR PERCUTANEOUS CATHETERIZATION

FIELD OF THE INVENTION

This invention relates to medical instruments and more particularly to the introduction of diagnostic or therapeutic catheters into vascular and other body compartments.

BACKGROUND OF THE PRIOR ART

Heretofore the procedure most frequently employed for the insertion of a large diameter catheter into a body vessel was the guide-wire technique of S. I. Seldinger which is described inter alia in Acta Radiology 39:368–376, 1953 and Br. Med. J. 2(6026):21–22,3 July 1976. Briefly, this procedure involves the execution of approximately ten carefully performed steps. First, the site area of skin is prepared and draped in the normal manner for percutaneous puncture. A local anesthetic is then administered as desired. Next, a small skin incision is made with a suitable scalpel. A thin wall puncture needle (stylette) of perhaps 16–18 gauge, surrounded by a small-bore cannula having an attached hub, is inserted through the skin into the vessel to be catheterized. Then the inner stylette is removed so that blood flows freely through the cannula and out the hub end. Next, the flexible end of a spring guide-wire is inserted through the cannula hub into the vessel. The cannula is then removed over the guide. Pressure is applied over the site of the puncture after the cannula is removed. A larger-bore "dummy" Teflon catheter and thin-walled sheath assembly is then inserted into the vessel over the spring guide. Next, the guide-wire and "dummy" catheter are grasped and removed together leaving the outer thin-walled sheath in the vessel. The diagnostic or therapeutic catheter is then fed through the sheath and into the vessel. Finally, the sheath is pulled out to the hub of the therapeutic catheter, or left in the vessel, as desired.

While the Seldinger technique has gained wide acceptance in the medical profession, a number of disadvantages are inherent in the procedure. The technique can be quite tedious even in the hands of the most experienced practitioner due to the required manipulation of the guide-wire and "dummy" catheter. Care must be taken not to withdraw the guide-wire into the cannula so as not to cause shearing of the guide. Intravascular knotting and separation of guide components have also been reported (Critical Care Medicine 9:347–348, April 1981). Vessel and organ perforation are other possible complications which one must be aware of when manipulating the guide-wire. It is also dangerous to advance the sheath and dilator together without a rotating motion, as otherwise the sheath may be damaged.

BRIEF SUMMARY OF THE INVENTION

I have devised a new catheterization device and technique that will effect the appropriate dilation of the established percutaneous channel in just one step following initial site preparation, thereby completely eliminating the need for guide-wires, large bore cannulas and the attendant manipulative procedures. In accordance with the principles of my invention, in one illustrative embodiment thereof, a novel needle-cannula combination is provided which is percutaneously inserted into the vessel through the prepared, draped and anesthetized skin site. The needle-cannula combination illustratively may have an overall outer diameter comparable to the overall outer diameter of the prior-art small bore puncture needle-and-cannula assembly used in the first steps of the above-described Seldinger technique. However, in an illustrative embodiment of my invention, the cannula of my needle-cannula combination is fabricated of shape memory alloy (SMA). The lumenal diameter of the cannula dilates after insertion into the body vessel as the material of which it is composed equilibrates to an appropriate predetermined temperature. The temperature, advantageously, is that which is within the range of encounterable blood vessel temperatures. Alternatively, the temperature may be artificially obtained by resistance heating, radiofrequency induction, temperature controlled solutions, whether heated or cooled, or by other methods, which do not endanger body tissue. After dilation of the cannula to the desired dimension has been obtained, the needle is withdrawn from the cannula and the required diagnostic or therapeutic catheter is inserted through the dilated cannula and into the vessel.

In one illustrative embodiment of my invention, the shape memory alloy cannula may advantageously be encased in an elastomeric sleeve whose lumenal diameter is stretched by the SMA material as it equilibrates to the desired temperature. Either the SMA cannula itself or the encasing sleeve may be terminated at its proximal end with a hub of suitable design to permit a connection to any of the standard types of intravenous (I.V.) tubing connectors. The hub may itself by comprised in whole or part of SMA.

BRIEF DESCRIPTION OF THE DRAWINGS

The foregoing objects and features of my invention may be better understood when the ensuing description is read together with the drawings, in which.

GENERAL DESCRIPTION OF THE ILLUSTRATIVE EMBODIMENTS

Figure 1:
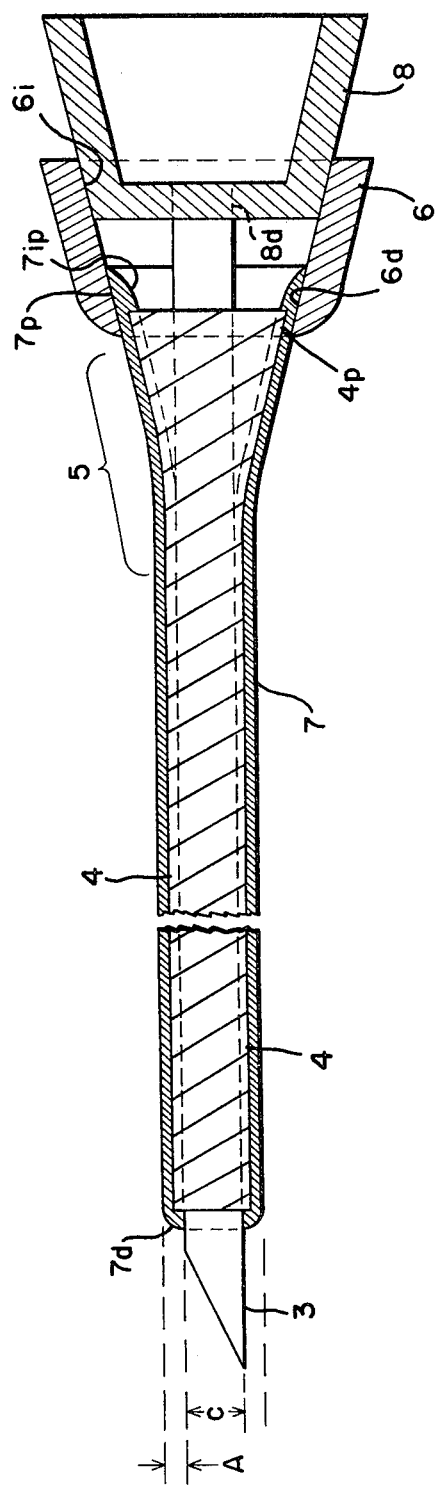
FIG. 1 is a longitudinal view in partial cross section of the needle and shape memory alloy cannula comprising one illustrative embodiment of my invention having an outer elastomeric sheath.

My catheterization apparatus and method makes use of the shape memory effect of certain metallic alloys. The shape memory effect is a phenomenon which is believed to have been first described by Greminger and Mooradian (1938) in their work with copper-zinc alloys. Later the shape memory effect was discovered in nickel-titanium alloys. Since then many alloys of the transition and precious metals have been shown to exhibit this phenomenon. Shape memory alloys exhibit the ability, when mechanically deformed at one temperature, to completely recover their original "parent" shape when subjected to a higher temperature. This recovery to a predetermined configuration results in a displacement and/or force which can be advantageously used in a variety of applications.

The shape memory effect is based on what is known as a martensite phase transformation. Shape memory alloys exist in two phases, one at a high temperature and another at a lower temperature. The high temperature phase is known as the austenite or beta-phase and is understood to be characterized by a body centered cubic symmetric crystal lattice. The low temperature phase is known as the martensite phase and is thought to be characterized by an orthorhombic crystal structure with much lower symmetry. For clarification, the following definitions will apply throughout:

$M_s$-The temperature at which the martensite begins to form on cooling the austenite crystal structure.

$M_f$-The temperature at which the transformation to martensite is complete.

$A_s$-The temperature at which the austenite begins to form on heating the martensite crystal structure.

$A_f$-The temperature at which the transformation to austenite is complete.

The shape memory effect can be produced in either "one-way", irreversible, or "two-way", reversible, modes. In the "one-way" mode, a specimen of shape memory alloy is fabricated to the desired configuration and then annealed at a high temperature to fix the shape. A martensite phase transformation then occurs as the specimen is cooled through the appropriate temperature range ($M_s \rightarrow M_f$). At this lower temperature the specimen can be deformed (reshaped) to any desired configuration. When the specimen is reheated to a temperature above the phase change ($A_s \rightarrow A_f$) but well below the annealing temperature, the alloy will return to its original "parent" shape. This recovery has been reported to be 100% complete if the deformation is limited to an internal strain of 3-9%. The temperature at which the memory is recovered is a function of the martensite transformation temperature which in turn depends on the composition of the alloy.

Shape memory alloys can also be fabricated to exhibit the property of trainability or reversibility ("two-way" effect). If a shape memory alloy is deformed beyond a minimum stain value while in its martensite phase, the original "parent" shape will be recovered on heating the specimen above the phase change as in the "one-way" effect. However, when the specimen is then cooled, the "parent" shape reverts back to the deformation (martensite) shape. Thus, a shape memory alloy can exhibit the memory phenomenon for two different configurations. In either mode, the shape memory alloy must undergo a martensite transformation in order to exhibit memory. The temperature of memory transformation is dependent on the composition of the alloy. The actual shape change is accompanied by a displacement, force, and the generation of an electromotive force as a function of temperature (or stress).

Referring now to FIG. 1, there is shown a conventional stylette puncture needle 3 which extends throughout the axial length of my needle-and-cannula combination. Snuggly surrounding stylette 3 is a tape-wound cannula 4 of shape memory alloy, surrounded by an elastomeric sheath 7. As depicted, cannula 4 is in its martensitic phase so that the overall outer diameter "G" comprising cannula 4 together with sheath 7 is of such size as to be convenient for introduction into a particular vascular or body compartment. The proximal end 5 of cannula 4, with elastomeric sheath 7, is flared such that the outer surface 7p of the proximal end of the elastomeric sheath 7 intimately engages the inner surface of the distal end 6d of hub 6. The inner surface 7ip of the proximal end of sheath 7 is molded with a lip which abuts the proximal, flared end of cannula 4. The distal tip 7d of the elastomeric sheath 7 is "molded" so as to minimize tissue trauma on insertion of the device.

At the proximal end of hub 6, the internal contour 6i may be shaped to accommodate the design of any of the variety of standard tubing connectors 8 that are commonly available. As depicted, the distal end 8d of connector 8 is bonded to the proximal end of needle 3. After needle 3 is removed, as hereinafter described, a standard I.V. connector may be inserted at the proximal end of Hub 6, as desired.

The inner diameter "c" of cannula 4 may be fabricated to any one of a variety of sizes so as to intimately envelop a particular size of conventional puncture needle 3, such, for example, as the commonly encountered 16 gauge needle. In any event, the overall outer diameter "G" of the combination ("C", plus double the wall thickness "A" of elastomeric sheath 7) is such as to be small enough, in each instance, to permit percutaneous entry into the particular vascular compartment with ease and with minimum tissue trauma and pain.

The pre-dilational dimensional considerations of the shape memory alloy cannula 4 fabricated of a helical ribbon are as follows:

Let:
a = thickness of ribbon
b = axial length of coil
c = internal diameter of coil
d = pitch
e = width of ribbon Post-dilation parameters are analogous and will be referred to as a', b', c', d', and e'.

Consider a cylinder of diameter c' around which a ribbon of thickness a' is wound. The internal diameter of the resulting coil is then c' and the outer diameter is c'+2a'. This represents the cross-sectional dimensions of a coiled ribbon fabricated in its austenite (beta phase) post-dilation phase. In order to mold the coil into its pre-dilation shape the ribbon must be wound tighter (around a cylinder of a smaller diameter) so that the internal diameter and outer diameter of the coil decrease. During this process the inner surface of the coiled ribbon is somewhat compressed and the outer surface is slightly stretched. There must then be a region within the thickness of the ribbon that is neither compressed nor stretched about which the strain can be calculated. This region is estimated to be at approximately a'/2. Therefore, given a coil of internal diameter, c', and thickness a'/2

$$\text{circumference} = \pi(c' + 2a'/2)$$

This represents the length of the outer surface of the coil for one revolution. Reducing, $$\text{circumference} = \pi(c' + a')$$

If the lumenal diameter is to accommodate a 9 French diagnostic or therapeutic catheter, c'=3.1 mm. Arbitrarily setting a'=0.15 mm the circumference of the coil at a distance a'/2 from the inner surface equals $$\pi(c' + a') = 3.25\pi \text{ mm}$$

in the post-dilation phase. The circumference of the coil at the inner surface equals 3.1 mm. If the lumenal diameter of the coil is to conform to an 18 gauge hypodermic needle in its pre-dilation phase, then c=1.27 mm. Therefore, $$\text{inner surface circumference} = 1.27\pi \text{ mm}$$

It follows then that $$\frac{3.1\pi}{1.27\pi} = 2.44$$

which represents the number of revolutions in the pre-dilated coil required to dilate to one full post-dilation revolution. The strain on the shape memory alloy helix at a distance $a'/2$ from the inner surface is then:

$$\text{strain} = \frac{2.44\pi(c+a) - \pi(c'+a')}{\pi(c'+a')}$$

$$= \frac{2.44(1.27+.15) - (3.1+.15)}{(3.1+.15)}$$

$$= 0.06609$$

Therefore the strain is approximately 6.61% in this particular plane. From the above equation it is possible to calculate the post-dilation lumenal diameter when $c, a, a'$, and strain (e) are known:

$$\frac{(c'/c)(c+a) - (c'+a')}{(c'+a')} = e$$

Given that $a' = a$:

$(c'/c)(c+a') - (c'+a') = e(c'+a')$ $c' + c'a'/c - c' - a' = ec' + ea'$ $c'a'/c - a' - ec' = ea'$ $c'a'/c - ec' = (1+e)a'$ $c'(a'/c - e) = (1+e)a'$ $c' = [(1+e)a'/(a'/c - e)]$

The following table lists the post-dilation internal diameters (c') with varying a, c, and e.

| Wall Thickness (a) | Pre-dilation I.D. (c) | | | | | | | | | | | |
|---|---|---|---|---|---|---|---|---|---|---|---|---|
| | 18 gauge (1.27 mm) Strain % | | | | 17 gauge (1.47 mm) Strain % | | | | 16 gauge (1.65 mm) Strain % | | | |
| | 6 | 7 | 8 | 9 | 6 | 7 | 8 | 9 | 6 | 7 | 8 | 9 |
| .14 mm | 2.95 | 3.72 | 5.00 | 7.54 | 4.21 | 5.94 | 9.92 | 29.13 | 5.97 | 10.00 | 31.19 | ∞ |
| .15 mm | 2.73 | 3.34 | 4.25 | 5.81 | 3.78 | 5.01 | 7.35 | 13.58 | 5.14 | 7.68 | 14.85 | 17.90 |
| .16 mm | 2.57 | 3.06 | 3.76 | 4.85 | 3.47 | 4.41 | 5.49 | 9.26 | 4.59 | 6.35 | 10.18 | 25.02 |
| .20 mm | 2.17 | 2.45 | 2.79 | 3.23 | 2.79 | 3.24 | 3.85 | 4.73 | 3.46 | 4.18 | 5.24 | 6.98 |

From the above table it is shown that a shape memory alloy cannula fabricated of a helical ribbon has significant dilational ability. The required dilation depends upon the application and as such, the dimensions can be adjusted accordingly. Assuming a strain of 6.6%, a helical ribbon of SMA material having an internal diameter of 1.27 mm (18 gauge) and wall thickness of 0.15 mm illustratively achieves a dilation adequate to pass through its lumen a 9 French diagnostic or therapeutic catheter.

The design of hub 6 shall conform to the constraints previously mentioned. The distal lumenal diameter of hub 6 can vary accordingly to the application. However, a 9 French diagnostic catheter is believed to be the largest diameter that should likely be encountered in practice. In this case, the distal lumen 6d of hub 6 would be approximately 3.1 mm in diameter. The proximal lumen 6i of the hub should be of such a dimension to adequately accommodate existing I.V. tubing connectors. If the conduit is designed to conform to a pre-dilation lumenal diameter of 1.27 mm (18 gauge), the distal lumen of the hub should be 3.1 mm in diameter to properly allow a 9 French diagnostic or therapeutic catheter to pass.

The material of sheath 7 must be compliant enough to allow the appropriate dilation of cannula 4 to occur once the apparatus has been admitted to the vascular or body compartment in question. An elastomeric material such as polyurethane is suggested as having the properties necessary to be an effective coating. The elastomeric material may be applied to the shape memory conduit by dipping, rolling, extrusion, molding or other process.

An illustrative design of the above-described introducer may incorporate a helical ribbon of nickel-titanium or other SMA having a wall thickness of approximately 0.15 mm; an internal diameter (I.D.) of 1.27 mm; a width of 3–4 mm, and an axial length of approximately 100 mm. The proximal end of this coil 4p may advantageously be conically tapered so that the outer periphery 7p of sheath 7 intimately contacts the distal lumen 6d of the hub 6. Alternatively, any other convenient method of bonding cannula 4 to hub 6 may be employed. The cannula 4 will envelop an 18 gauge hypodermic needle and upon proper vascular insertion of this pre-sterilized device, the cannula 4 dilates to an I.D. of approximately 3.1 mm thereby allowing a 9 French diagnostic or therapeutic catheter to be passed through its channel.

In summary, the catheterization device of my invention greatly simplifies the introduction technique. After appropriate site preparation the needle-cannula combination is simply inserted. As the cannula equilibrates to the temperature of the body compartment into which it has been inserted, it dilates to a predetermined internal diameter. The hypodermic puncture needle (stylette 3) is then withdrawn leaving cannula 4 in place. A diagnostic or therapeutic catheter (not shown) may then be passed through the hub of the dilated cannula 4. Cannula 4 may then be withdrawn or left in place.

It should be understood that the cannula 4 may be comprised of any appropriately fabricated SMA material necessary to achieve the required dilation. Any suitable pitch or cross-section may be utilized. Alternatively, the cannula may comprise a tubular mesh (not shown). Sheath 7 may be dispensed with, in which case the proximal coil 5 may be shaped to the contour of a conventional hub 6.

Figure 2:
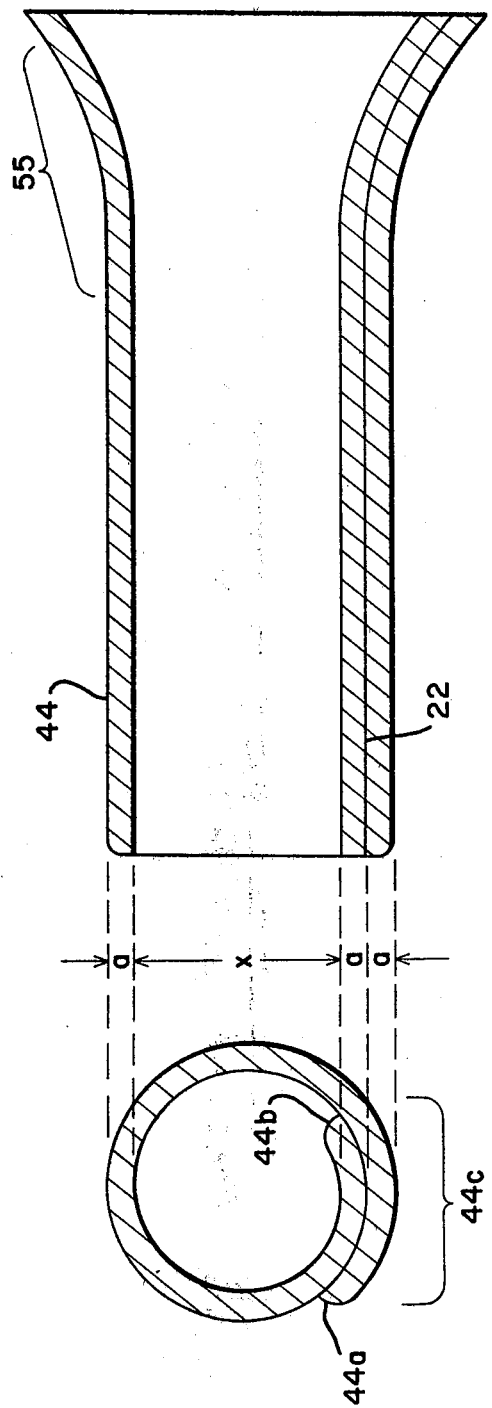
FIG. 2 is a distal cross section and a longitudinal section of a differently fabricated SMA cannula without needle or elastomeric sheath.

Referring to FIG. 2, an alternative cannula construction is shown. An SMA cylinder 44 having a helical pitch of zero exhibits a longitudinal slit 22 in the region 44c where the coil ends 44a and 44b overlap each other. Upon equilibration to the desired temperature, cylinder 44 expands, its internal diameter X increasing such that coil ends 44a and 44b approach each other. The proximal end 55 of cylinder 44 is advantageously flared in a manner analogous to that of cannula 4 of FIG. 1. An elastomeric sheath (not shown) may also be employed analogous to sheath 7 of FIG. 1. It is apparent that the overlap region 44c will have a double wall thickness ("a"+"a") at the wall interface. It should also be apparent that this double wall thickness may be lessened or eliminated as desired by tapering of the wall thickness in this region. Further and other modifications will be apparent to those of skill in the art.

What is claimed is:

1. A device for introducing a large bore diagnostic or therapeutic catheter into a body compartment or vessel, comprising a thin wall cannula of shape memory alloy having an inner diameter fashioned to embrace the shank of a hypodermic needle, said cannula exhibiting, in its martensitic phase, an outer diameter convenient for percutaneous puncture of a body compartment or vessel and exhibiting, in its austentitic beta-phase, an inner diameter to slidably accomodate the outer diameter of said large bore diagnostic or therapeutic catheter, and a dilatable elastomeric cylindrical sheath deployed over the surface of said cannula.

2. A device according to claim 1 wherein said cannula is fabricated of shape memory alloy exhibiting said martensitic phase in the temperature range of 28° C. to 35° C. and said austentitic phase in the range of 37° C. to 41° C.

3. A device according to claim 1 wherein said cannula is flared at its proximal end to form a hub having a lumen to accomodate the unrestricted passage of large bore diagnostic/therapeutic catheters, said hub having an outer surface which may be grasped to facilitate removal of the cannula from said body compartment or vessel after said large bore catheter has been inserted.

4. A device according to claim 1 further comprising a dilatable elastomeric cylindrical sheath, deployed over a surface of said cannula.

5. A device according to claim 3 wherein said sheath is flared at its proximal end to accomodate an intravenous tubing connection.

6. A device according to claim 1 wherein said cannula comprises a shape memory alloy cylinder in the form of a helical ribbon having a pitch substantially equal to its longitudinal dimension such that upon transformation from the martensitic to the austentitic phase said shape memory alloy cannula will effectively dilate to allow the unrestricted longitudinal passage of a large-bore diagnostic or therapeutic catheter.

7. A device according to claim 1 wherein said shape memory alloy cylinder comprises a hollow cylindrical mesh.

8. A device according to claim 1 wherein said shape memory alloy cannula is fabricated of helically-wound wire.

9. A device according to claim 1 wherein dilation will be achieved using the "two-way" shape memory effect such that the device will exist in its austentitic phase as a small bore needle-cannula combination so as to effect simple percutaneous insertion and, upon cooling to its martensitic phase, said device will effectively dilate.

10. A device according to any of claim 1 wherein said plastic sheath is fabricated of sufficiently rigid material to withstand premature dilational transformation prior to insertion in a body compartment which may occur as a result of unexpected high environmental temperatures encountered during shipping, storage, or sterilization.

* * * * *